(12) United States Patent
Koike

(10) Patent No.: US 7,262,857 B2
(45) Date of Patent: Aug. 28, 2007

(54) DEVICE FOR MEASURING IMMUNOCHROMATOGRAPHY TEST PIECE

(75) Inventor: Takashi Koike, Hamamatsu (JP)

(73) Assignee: Hamamatsu Photonics K.K., Shizuoka (JP)

(*) Notice: Subject to any disclaimer, the term of this patent is extended or adjusted under 35 U.S.C. 154(b) by 58 days.

(21) Appl. No.: 10/546,828

(22) PCT Filed: Feb. 19, 2004

(86) PCT No.: PCT/JP2004/001921

§ 371 (c)(1),
(2), (4) Date: Aug. 25, 2005

(87) PCT Pub. No.: WO2004/077028

PCT Pub. Date: Sep. 10, 2004

(65) Prior Publication Data

US 2006/0197955 A1    Sep. 7, 2006

(30) Foreign Application Priority Data

Feb. 26, 2003    (JP)    ............................. 2003-049861

(51) Int. Cl.
G01N 21/55    (2006.01)
G01N 21/00    (2006.01)
G01J 3/46    (2006.01)

(52) U.S. Cl. .................. 356/445; 356/344; 356/402

(58) Field of Classification Search ......... 356/445–446
See application file for complete search history.

(56) References Cited

U.S. PATENT DOCUMENTS 5,654,803 A    8/1997  Howard, III et al. ....... 356/446
6,819,422 B2 * 11/2004  Yamauchi ................... 356/344

FOREIGN PATENT DOCUMENTS

JP    50-003683 A    1/1975
JP    59-120939 A    1/1984
JP    11-083745 A    3/1999
JP    2002-098631 A    4/2002

* cited by examiner

Primary Examiner—Gregory J. Toatley, Jr.
Assistant Examiner—Iyabo S Alli
(74) Attorney, Agent, or Firm—Drinker Biddle & Reath LLP

(57) ABSTRACT

A measuring device 1 for immunochromatographic test strip 5a is configured to irradiate measurement light onto the immunochromatographic test strip 5a and to measure light from the immunochromatographic test strip 5a, and is provided with a photodiode 3a for receiving the light from the immunochromatographic test strip 5a, and a measuring head 4 disposed between the immunochromatographic test strip 5a and the photodiode 3a and having a plurality of light paths 3b, 3b, 3b, 3b for guiding part of the light from the immunochromatographic test strip 5a to the photodiode 3a. The measuring head 4 functions as a light shielding member for shielding against unwanted light reflected on the immunochromatographic test strip 5a. The plurality of light paths 3b, 3b, 3b, 3b are juxtaposed along a direction in which a colored portion 8 of line shape formed on the immunochromatographic test strip 5a extends.

12 Claims, 9 Drawing Sheets

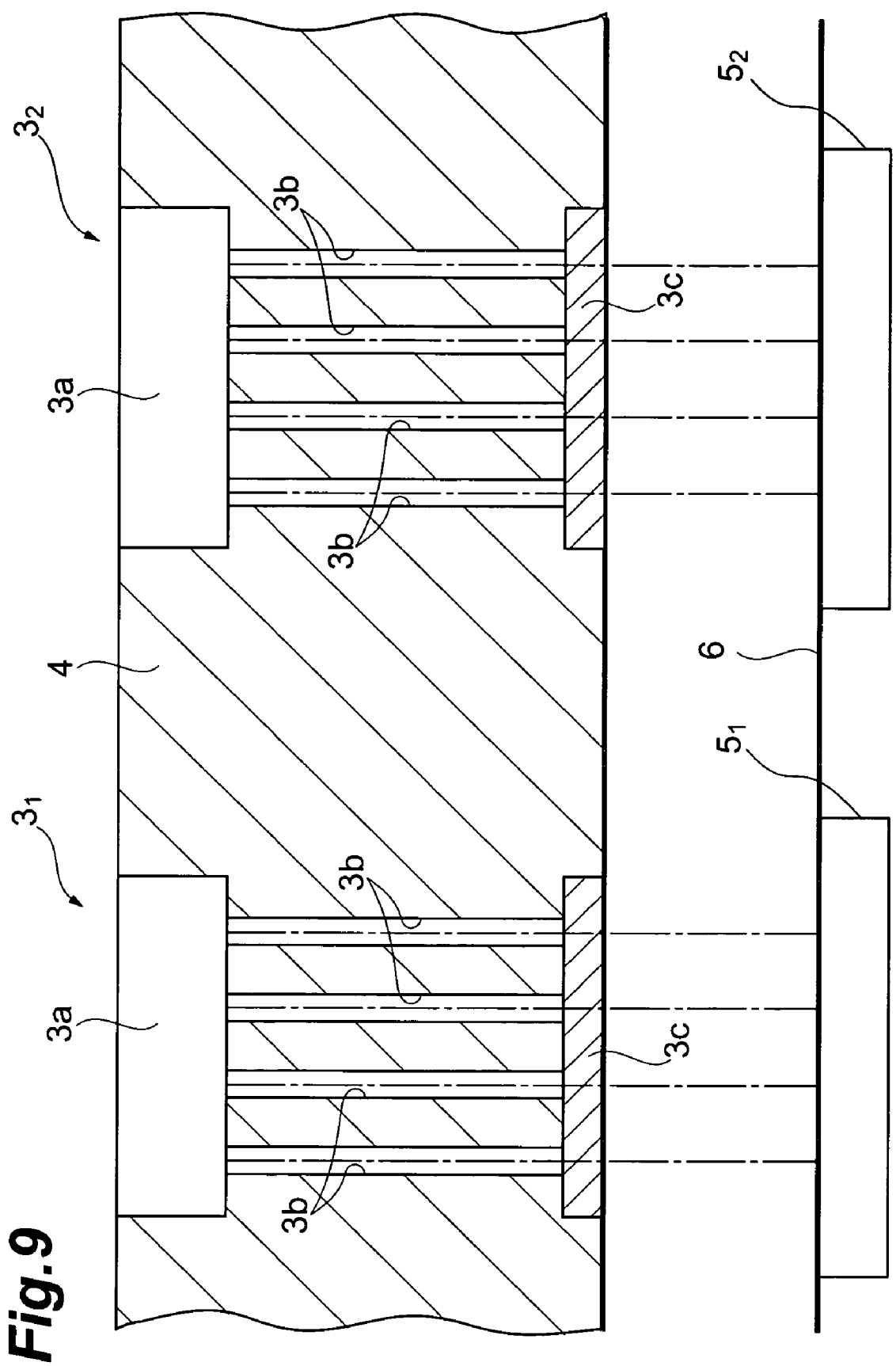

DEVICE FOR MEASURING IMMUNOCHROMATOGRAPHY TEST PIECE

TECHNICAL FIELD

The present invention relates to a measuring device for immunochromatographic test strip.

BACKGROUND ART

A description will be given of the immunochromatographic assay. An immunochromatographic test strip is a test strip preliminarily coated with a bandlike coating of an antibody (or antigen) which brings about an antigen-antibody reaction with an antigen (or antibody) in analyte (sample), at a specific location on the test strip. After the analyte is applied to the immunochromatographic test strip, the antigen (or antibody) in the analyte is dissolved into a developing solution and migrates on the test strip, and the antigen (or antibody) in the analyte comes to bring about the antigen-antibody reaction at the location of the antibody (or antigen) coating on the immunochromatographic test strip, to be trapped. Since an amount of the antigen (or antibody) thus trapped is the total amount of the antigen (or antibody) in the analyte, the total amount of the antigen (or antibody can be measured by optical measurement in a way of labeling the antigen (or antibody) in the analyte with a dye and measuring the absorbance or the like thereof. The immunochromatographic assay is a method enabling quantitative determination of even an extremely fine amount when compared with the ordinary color test methods.

One of known devices for measuring a concentration of a specific substance in analyte from an immunochromatographic test strip after development and coloring of the analyte is a device configured to reflect measurement light emitted from an LED, on the immunochromatographic test strip and to measure the reflected light with a photodiode through one hole for guiding the reflected light (e.g., reference is made to Patent Document 1).

[Patent Document 1] Japanese Patent Application Laid-Open No. 11-83745 (p4)

DISCLOSURE OF THE INVENTION

Incidentally, a colored portion of line shape on an immunochromatographic test strip sometimes exhibits a considerable difference of density depending upon positions thereof. This can cause such a situation that the level of color is estimated as a value smaller than actual if the reflected light is measured from a location where the density of the color in the colored portion is low (the degree of the color is low). If the reflected light is measured from a location where the density of the color in the colored portion is high (the degree of the color is high), the level of the color will be estimated as a value larger than actual.

If the diameter of the hole is increased in order to avoid such error, the photodiode will also measure the reflected light from the regions other than the colored portion and could cause a large error in the measurement result.

The present invention has been accomplished in view of the above-described respects, and an object of the present invention is to provide a measuring device for immunochromatographic test strip capable of accurately measuring the level of the color on the immunochromatographic test strip.

In order to achieve the above object, an immunochromatographic test strip measuring device according to the present invention is a measuring device for immunochromatographic test strip, arranged to irradiate measurement light onto an immunochromatographic test strip and to measure light from the immunochromatographic test strip, the measuring device comprising: a photodiode for receiving the light from the immunochromatographic test strip; and a light shielding member provided between the immunochromatographic test strip and the photodiode, and having a plurality of light paths for guiding part of the light from the immunochromatographic test strip to the photodiode, wherein the plurality of light paths are juxtaposed along a direction in which a colored portion of line shape formed on the immunochromatographic test strip extends.

In the measuring device for immunochromatographic test strip according to the present invention, the light from the immunochromatographic test strip is guided to the photodiode by the plurality of light paths provided in the light shielding member. In this configuration, even if the colored portion on the immunochromatographic test strip has a density difference, the photodiode will measure the light guided through the light paths from a plurality of different locations of the colored portion. This results in averaging densities and thus permits the level of the color of the colored portion to be measured more accurately. Since the plurality of light paths are juxtaposed along the colored portion of line shape on the immunochromatographic test strip, the level of the color of the colored portion can be measured with certainty.

A width of each light path is preferably not more than a width of the colored portion of line shape. In this case, each light path is able to appropriately guide the light from the colored portion to the photodiode. This prevents the photodiode from measuring the unwanted light except for the light from the colored portion, whereby the degree of the color of the colored portion can be measured more accurately.

Each light path is preferably a hole portion formed in the light shielding member. In this case, the light from the immunochromatographic test strip can be guided to the photodiode by the simple configuration wherein the hole portions are provided in the light shielding member.

An inside diameter of each hole portion is preferably not more than a width of the colored portion of line shape. In this case, each hole portion is able to appropriately guide the light from the colored portion to the photodiode.

The number of photodiodes is preferably set to be not less than 1 and not more than the number of the light paths. In this case, density differences depending upon locations of the colored portion of line shape can be appropriately evaluated without increase in the number of photodiodes.

The light from the immunochromatographic test strip is preferably reflected light of the measurement light irradiated onto the immunochromatographic test strip. In this case, an irradiation optical system for irradiating the measurement light and a detection optical system for measuring the reflected light can be arranged on one surface side of the immunochromatographic test strip.

The light from the immunochromatographic test strip is preferably transmitted light of the measurement light irradiated onto the immunochromatographic test strip. In this case, the irradiation optical system for irradiating the measurement light and the detection optical system for measuring the transmitted light can be arranged so as to interpose the immunochromatographic test strip between them.

The immunochromatographic test strip is preferably moved relative to a detection optical system including the photodiode and the light paths, in parallel with a moving direction of an antigen or antibody on the immunochromatographic test strip. In this case, the absorbance of the colored portion can be measured by comparison with a non-colored portion.

A plurality of detection optical systems each including the photodiode and the light paths are preferably juxtaposed. In this case, one or more immunochromatographic test strips can be simultaneously evaluated as to the level of the color of the colored portion, whereby it is feasible to increase efficiency of readout of immunochromatographic test strips.

Another immunochromatographic test strip measuring device according to the present invention is a measuring device for immunochromatographic test strip comprising: a table on which an immunochromatographic test strip is to be mounted; a light emitting diode for emitting light toward the table; a photodiode for receiving light coming from the table; and a light shielding member disposed between the table and the photodiode, wherein the light emitting diode and the photodiode move relative to the table in a predetermined direction, and wherein a plurality of light paths penetrating the light shielding member from the table side to the photodiode side are formed in juxtaposition in a direction intersecting with the predetermined direction, in the light shielding member.

BRIEF DESCRIPTION OF THE DRAWINGS

FIG. 9 is a schematic perspective view for explaining a configuration of a measuring device for immunochromatographic test strip according to a third embodiment.

BEST MODES FOR CARRYING OUT THE INVENTION

Preferred embodiments of the measuring device for immunochromatographic test strip according to the present invention will be described below in detail with reference to the drawings. The same elements, or elements with the same functionality will be denoted by the same reference symbols in the description, without redundant description.

First Embodiment

Figure 1:
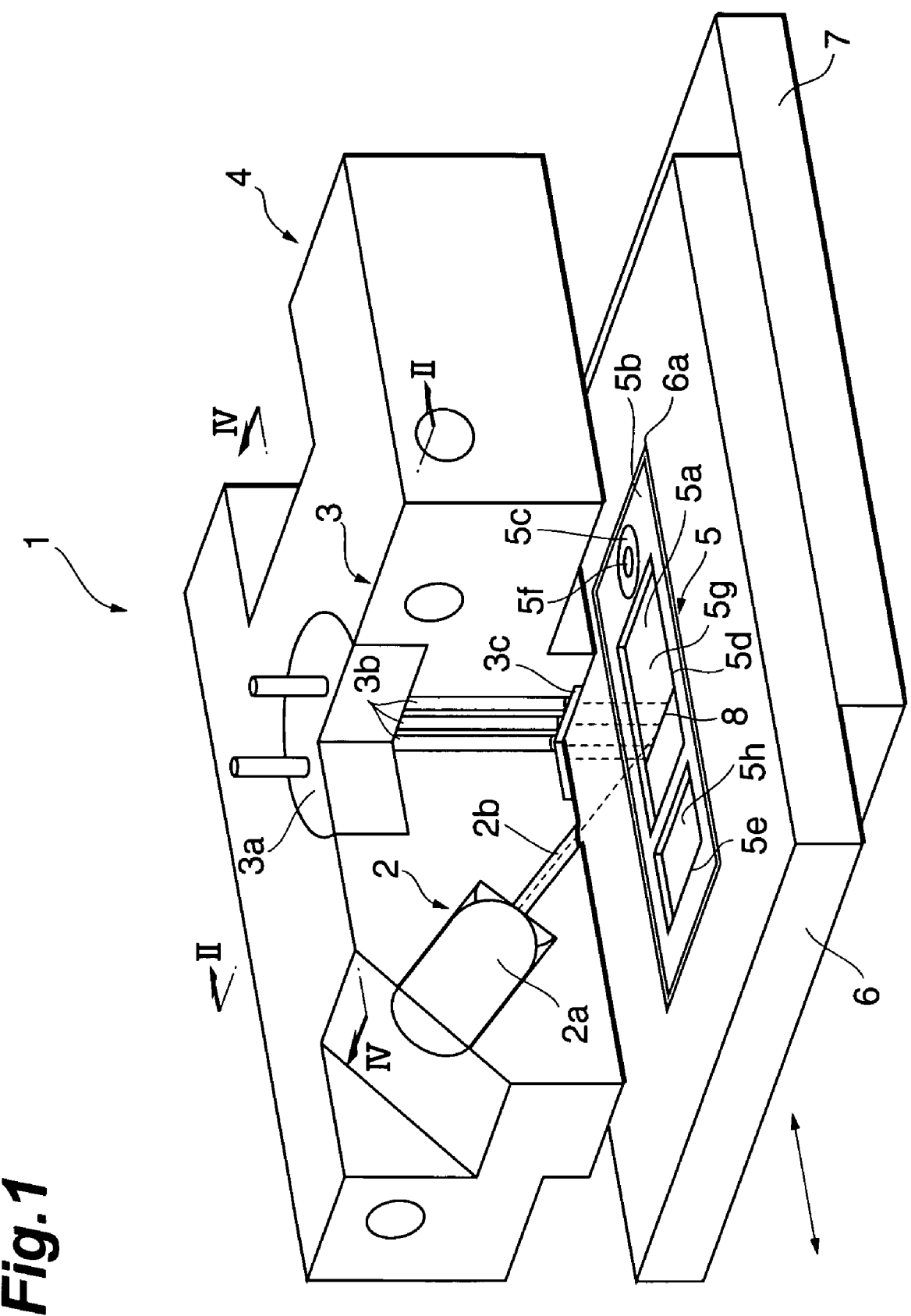
FIG. 1 is a schematic perspective view for explaining a configuration of a measuring device for immunochromatographic test strip according to a first embodiment.
Figure 2:
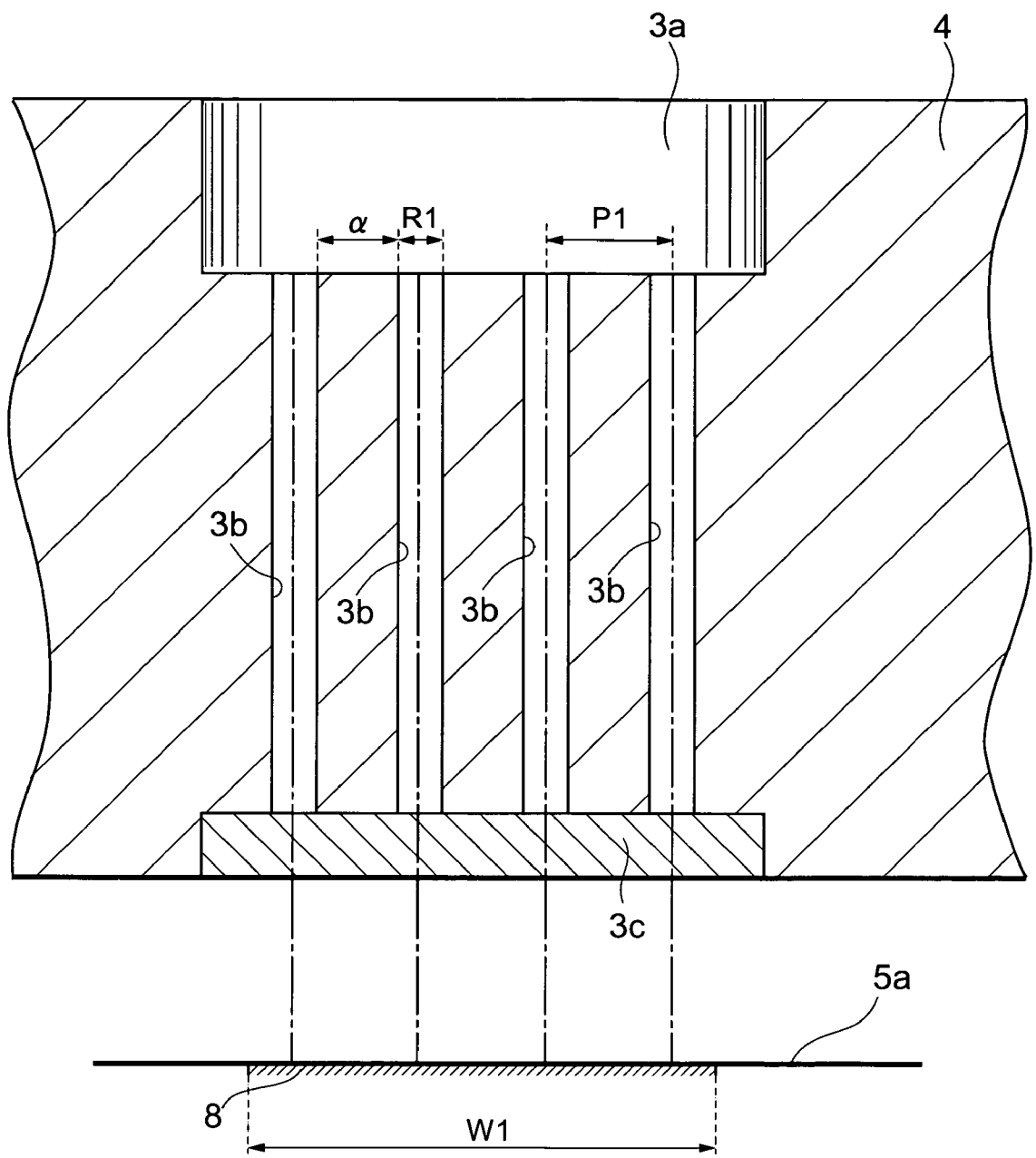
FIG. 2 is a schematic view showing a sectional configuration along line II-II in FIG. 1.

FIG. 1 is a schematic perspective view for explaining a configuration of a measuring device for immunochromatographic test strip according to the first embodiment. FIG. 2 is a schematic view showing a sectional configuration along line II-II in FIG. 1. In FIG. 1, measuring head 4 and others, described hereinafter, are illustrated as partly broken, for convenience sake of description.

The measuring device 1 has a measuring head 4 provided with an irradiation optical system 2 and a detection optical system 3, a sample table 6 for fixing an immunochromatographic test strip 5a, and a moving table 7. The irradiation optical system 2 irradiates measurement light onto the immunochromatographic test strip 5a. The detection optical system 3 detects light from the immunochromatographic test strip 5a under irradiation with the measurement light. The sample table 6 is opposed to the measuring head 4 with a predetermined clearance between them. The moving table 7 supports the sample table 6 and moves the sample table 6 in parallel with a moving direction of an antigen or antibody on the immunochromatographic test strip 5a. The moving table 7 has a sliding mechanism, a motor, etc. (not shown) provided on a contact surface with the sample table 6.

The irradiation optical system 2 includes an LED 2a as a light source for irradiating the measurement light onto the surface of the immunochromatographic test strip 5a, and a hole 2b formed in the measuring head 4. The hole 2b guides the measurement light emitted from the LED 2a, to the surface of the immunochromatographic test strip 5a.

The detection optical system 3 includes a photodiode 3a, four light guide holes 3b, 3b, 3b, 3b (cf. FIG. 2) formed in the measuring head 4, and a protection plate 3c. Each light guide hole 3b, 3b, 3b, 3b is formed so as to penetrate the measuring head 4 from the side of sample table 6 to the side of photodiode 3a. Each light guide hole 3b, 3b, 3b, 3b functions as a light path for guiding part of the light reflected on the surface of immunochromatographic test strip 5a, to the photodiode 3a. The protection plate 3c is a platelike member with a light transmitting property covering light inlets of the light guide holes 3b, 3b, 3b, 3b in order to prevent contaminants or the like from entering the light guide holes 3b, 3b, 3b, 3b. These light guide holes 3b, 3b, 3b, 3b are arranged in parallel with a colored portion 8 of line shape on the immunochromatographic test strip 5a and at equal intervals, in the measuring head 4.

In FIG. 2, let P1 be the pitch of light guide holes 3b, α a be the thickness of the wall between light guide holes 3b, and W1 be the length of the colored portion 8 of line shape.

There are no particular restrictions on the shape of the light guide holes 3b, 3b, 3b, 3b as long as they can guide part of the light from the colored portion 8 on the immunochromatographic test strip 5a to the photodiode 3a. For example, they may be thin pipes or optical fibers. In the present embodiment the sectional shape of light guide holes 3b, 3b, 3b, 3b is circular, but it may be, for example, polygonal.

The measuring head 4 is made of a material with a light shielding property to shield against light (e.g., metal or the like), and functions as a light shielding member for shielding against unwanted light reflected on the immunochromatographic test strip 5a. In the present embodiment the measuring head 4 is made of the material with the light shielding property and also serves as the light shielding member, but the measuring head 4 may be constructed separately from the light shielding member; for example, it is also possible to adopt a configuration wherein a light shielding plate of plate shape is installed so as to block optical paths of unwanted light from the immunochromatographic test strip 5a.

An immunochromatographic unit 5 is provided with an immunochromatographic test strip 5a of rectangular shape made of a material such as a nitrocellulose membrane or filter paper. This immunochromatographic test strip 5a is held in a casing 5b of rectangular shape on a plan view. The casing 5b is provided with an analyte drop window 5c, an observation window 5d, and a control window 5e along the longitudinal direction thereof.

The immunochromatographic test strip 5a has an analyte drop portion 5f provided at a position corresponding to the analyte drop window 5c, and detection portions 5g, 5h provided at positions corresponding to the observation window 5d and the control window 5e.

The detection portion 5g is coated with antibodies (or antigens) that react with respective partner antigens (or antibodies) in analyte, the antibodies (or antigens) being immobilized in line shape (or band shape). The immunochromatographic unit 5 is fitted in a recess 6a corresponding to the size of the casing 5b provided on the sample table 6, to be held therein.

An analyte is delivered dropwise through the analyte drop window 5c onto the analyte drop portion 5f. An antigen (or antibody) in the analyte binds to a label dye, and the combination of the antigen (or antibody) in the analyte with the label dye, and the non-reacted label dye move in the longitudinal direction of the immunochromatographic test strip 5a.

Let us suppose that the analyte contains an antigen and the antigen brings about an antigen-antibody reaction with the detection portion 5g. As the analyte moves, the antigen in the analyte specifically reacts with the partner antibody immobilized in the detection portion 5g, to form a colored portion 8 of line shape colored with the label dye in the reacted detection portion 5g. This colored portion 8 is formed as extending in the direction perpendicular to the moving direction of the antigen (or antibody) in the analyte on the immunochromatographic test strip 5a, and can be observed through the observation window 5d.

The sample table 6 is a platelike member functioning to hold the immunochromatographic unit 5 in the recess 6a. When the immunochromatographic unit 5 is set on the sample table 6, the immunochromatographic test strip 5a is mounted on the sample table 6. The sample table 6 and the measuring head 4 are arranged with a certain clearance between them. A moving mechanism such as a sliding mechanism is incorporated on contact surfaces between the sample table 6 and the moving table 7, so that the sample table 6 can move at a predetermined speed in parallel with the moving direction of the antigen or antibody on the immunochromatographic test strip 5a, while holding the immunochromatographic unit 5, through operation of a moving means such as a motor not shown.

Subsequently, the operation of the measuring device 1 for immunochromatographic test strip will be described.

After passage of a predetermined reaction time since dropwise delivery of the analyte onto the analyte drop portion 5f of the immunochromatographic unit 5 held in the recess 6a, the sample table 6 starts to slide at a predetermined speed on the moving table 7 and measurement is initiated. Namely, the LED 2a emits the measurement light onto the moving immunochromatographic test strip 5a and the reflected light from the immunochromatographic test strip 5a is guided by the four light guide holes 3b, 3b, 3b, 3b to be measured by the photodiode 3a.

Figure 3:
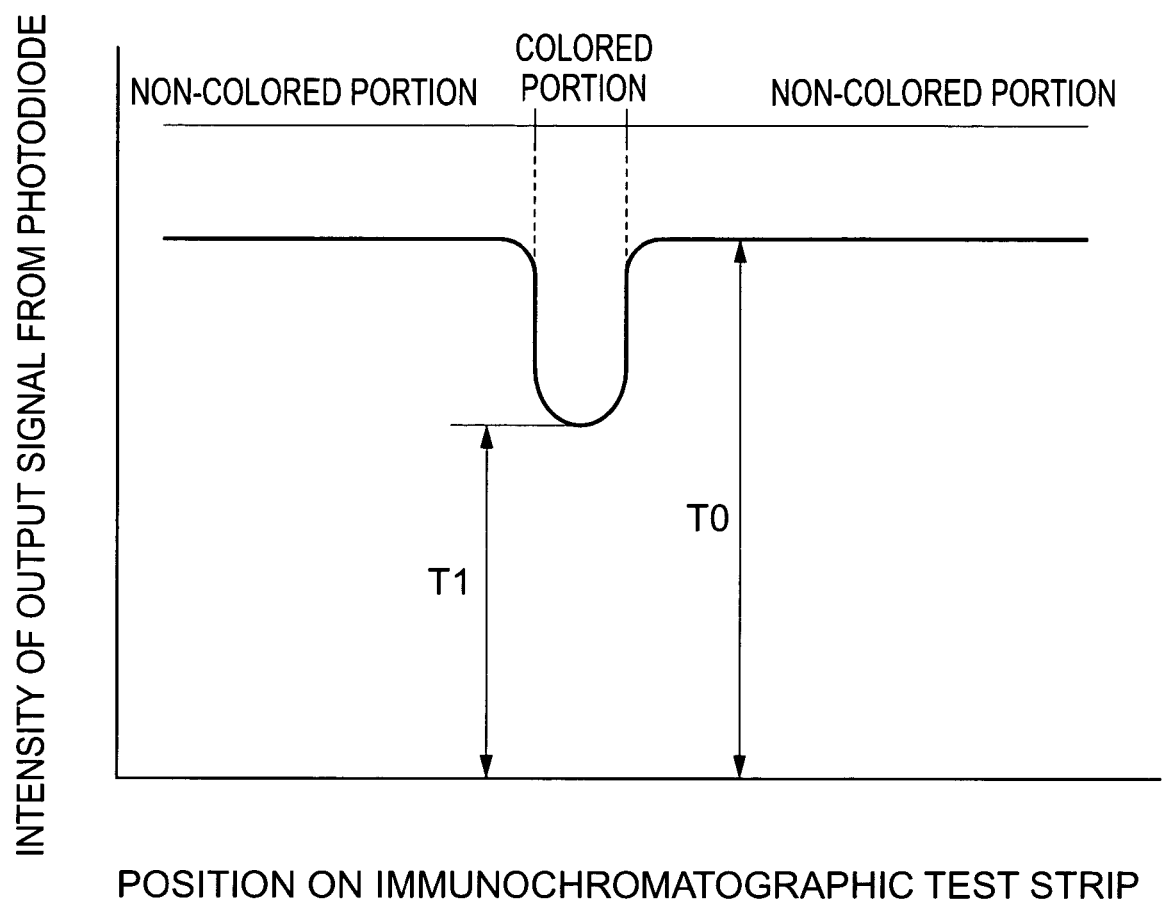
FIG. 3 is a chart showing an absorption profile of reflected light from an immunochromatographic test strip.

As an output signal from the photodiode 3a is measured with movement of the immunochromatographic test strip 5a as described above, the measuring device provides, for example, an absorption profile of light from the immunochromatographic test strip 5a as shown in FIG. 3. An absorbance is calculated in accordance with the ordinary method from a ratio of intensity T0 of the output signal from a non-colored portion to intensity T1 (level of color) of the output signal from the colored portion 8 in the resultant absorption profile. Then this absorbance is compared with a calibration curve prepared in advance to determine a concentration of the antigen or antibody in the analyte.

Subsequently, the shape of the light guide holes 3b, 3b, 3b, 3b will be described below in detail with reference to FIGS. 2, 4, and 5.

Figure 4:
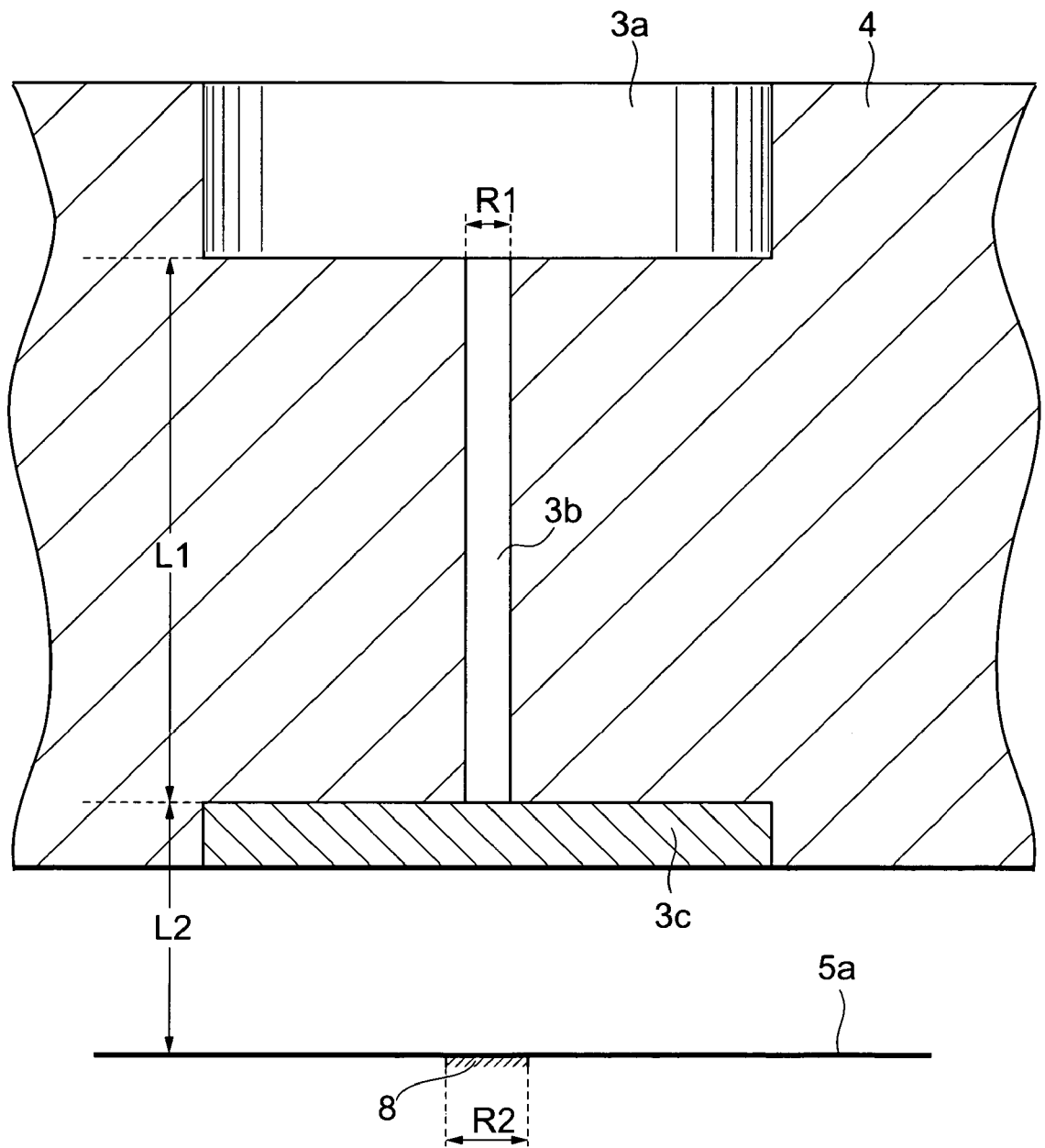
FIG. 4 is a schematic view showing a sectional configuration along line IV-IV in FIG. 1.
Figure 5:
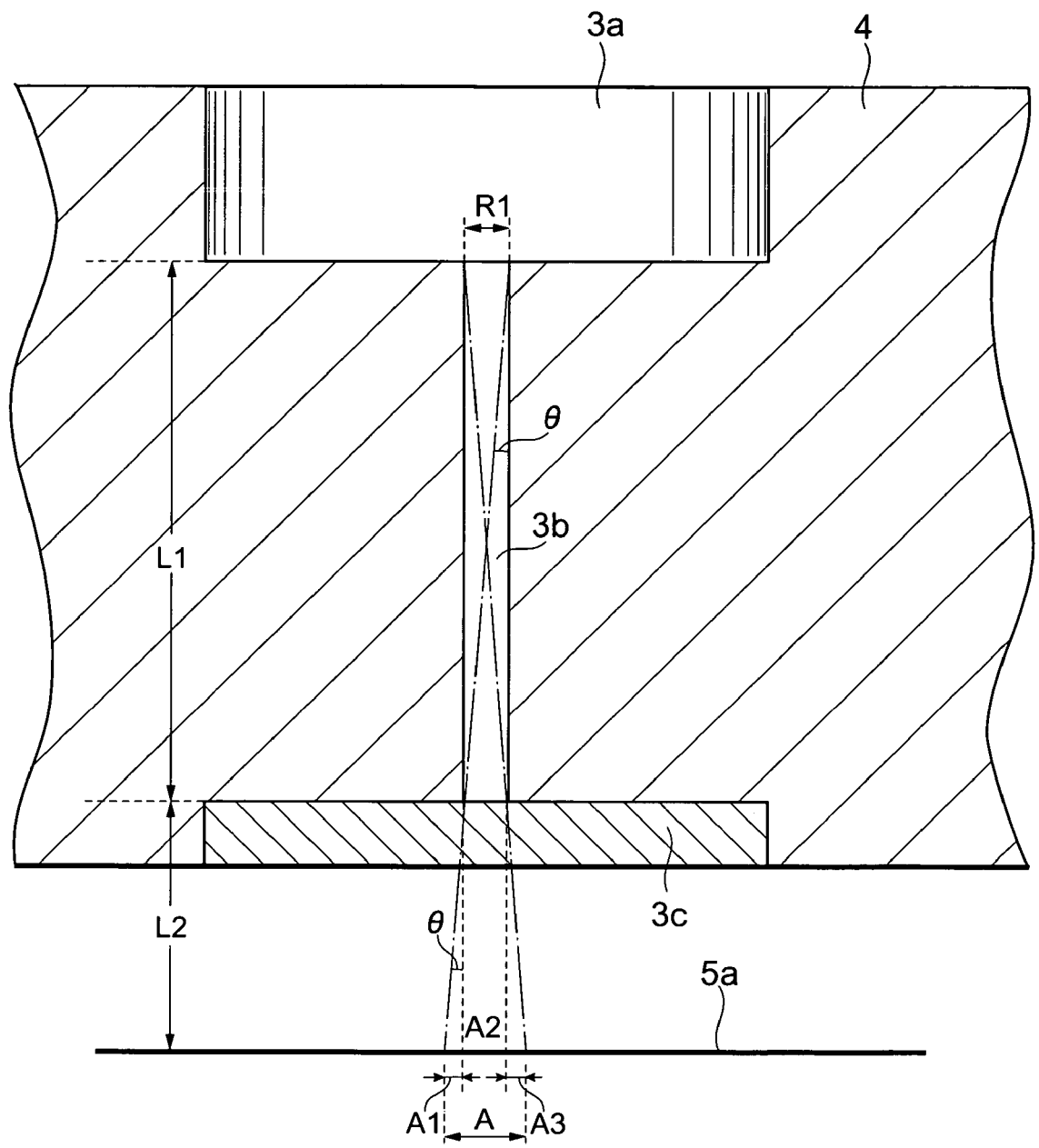
FIG. 5 is an illustration for explaining a setting range of inside diameter of light guide holes.

FIG. 4 is a schematic diagram showing a sectional configuration along line IV-IV in FIG. 1. In FIG. 4, R1 represents the inside diameter of the light guide hole 3b, L1 the length of light guide hole 3b, L2 the distance from the light inlet of light guide hole 3b to the immunochromatographic test strip 5a, and R2 the width of the colored portion 8 of line shape.

Let us consider a condition to be met by the inside diameter R1 of light guide hole 3b in this situation. The light guide hole 3b functions to guide the light reflected by the colored portion 8, to the photodiode 3a. In order to more accurately measure the level of the color in the colored portion 8, the light entering the light guide hole 3b is required to include no mixture of the light reflected on the non-colored portion. This requires the inside diameter R1 to satisfy Formula (1) below, as a condition for the inside diameter R1 of the light guide hole 3b.

$$R2 \geq R1 + 2 \times R1 \times L2/L1 \tag{1}$$

The right-hand side in this Formula (1) above indicates the width of the immunochromatographic test strip Sa corresponding to the width of the light allowed to enter the light guide hole 3b among the light from the immunochromatographic test strip 5a. Referring to FIG. 5, the light entering the light guide hole 3b is light from a region A on the immunochromatographic test strip 5a. The width of region A2 is R1 from FIG. 5, and the width of regions A1 and A3 is determined as L2×tanθ, i.e., L2×R1/L1. Therefore, the width of the region A is obtained as R1+2×R1×L2/L1. In order to prevent the light from the non-colored portion from entering the light guide hole 3b, it is necessary to keep the width of the region A not more than the width R2 of the colored portion 8, and thus Formula (1) above needs to be satisfied.

Formula (1) is derived by ignoring refraction of light in the protection plate 3c, because the protection plate 3c is formed in a sufficiently small thickness.

When the inside diameter R1 of light guide hole 3b is set as defined by Formula (1), the measuring device 1 for immunochromatographic test strip is able to take only the light from the colored portion 8 into the light guide hole 3b and to accurately measure the level of the color of the colored portion 8.

The inside diameter R1 of light guide hole 3b is preferably set as large as possible within the range satisfying Formula (1). This configuration increases the amount of reception of the light from the colored portion 8, so as to improve the detection sensitivity.

Next, let us consider a relation between L1 and L2. There are no particular restrictions on the ratio of L1 and L2, and they may be determined together with R1 so as to satisfy Formula (1). However, where L1<L2, if Formula (1) is solved on the assumption that the width R2 of the colored portion 8 of line shape is approximately 1 mm, the inside diameter R1 of light guide hole 3b is not more than about 0.3 mm. For this reason, the difficulty is high in processing the light guide hole 3b, and thus the relation of L1<L2 is not preferred.

If L1>L2 and as L1/L2 increases, the inside diameter R1 of light guide hole 3b can be set larger from Formula (1), and thus it is preferred. Incidentally, the distance L2 between the immunochromatographic test strip 5a and the light inlet of the light guide hole 3b needs to be approximately several mm in practice, for example, because the measurement light has to be irradiated onto the immunochromatographic test strip 5a. Therefore, a large ratio of L1/L2 (e.g., L1/L2=5) will result in increasing the length L1 of the light guide hole 3b too much, so as to increase the difficulty in processing the light guide hole 3b, and it is thus not desired.

In view of these, the relation of L1 and L2 is preferably L1/L2 in the range of about 2 to 3.

L1 and L2 are preferably determined to satisfy L1/L2 of about 2 to 3 and are as small as possible within the range satisfying Formula (1). The reason is that the quantity of light measured by the photodiode 3a decreases in inverse proportion to the square of the distance. The decrease of L1 and L2 leads to decrease in the distance between the photodiode 3a and the immunochromatographic test strip 5a, so as to increase the amount of reception of the light from the colored portion 8, thereby improving the detection sensitivity.

Next, the number of light guide holes 3b to be set will be described below in detail with reference to FIGS. 2 and 6.

In FIG. 2, let P1 be the pitch of light guide holes 3b, a be the thickness of the wall between light guide holes 3b, and W1 be the length of the colored portion 8 on a line.

Let us consider the number N of light guide holes 3b that can be provided in the measuring head 4. The light guide holes 3b function to guide the light reflected by the colored portion 8, to the photodiode 3a. In order to more accurately measure the level of the color in the colored portion 8, the light entering the light guide holes 3b is required to include no mixture of the light reflected from the non-colored portion. For this reason, it is necessary to satisfy Formula (2) below, as a condition for the number N of light guide holes 3b to be provided in the measuring head 4.

$$N \leq (W1 - 2 \times R1 \times L2/L1)/(R1 + \alpha) \quad (2)$$

Here "R1+α" being the denominator on the right-hand side in Formula (2) above is the pitch P1 of light guide holes 3b. The numerator "W1−2×R1×L2/L1" on the right-hand side in Formula (2) indicates a length where the light guide holes 3b can be set (which is equivalent to the length of the region B2 in FIG. 6), on the assumption that the light from the colored portion 8 having the length W1 all enters the light guide holes 3b.

Figure 6:
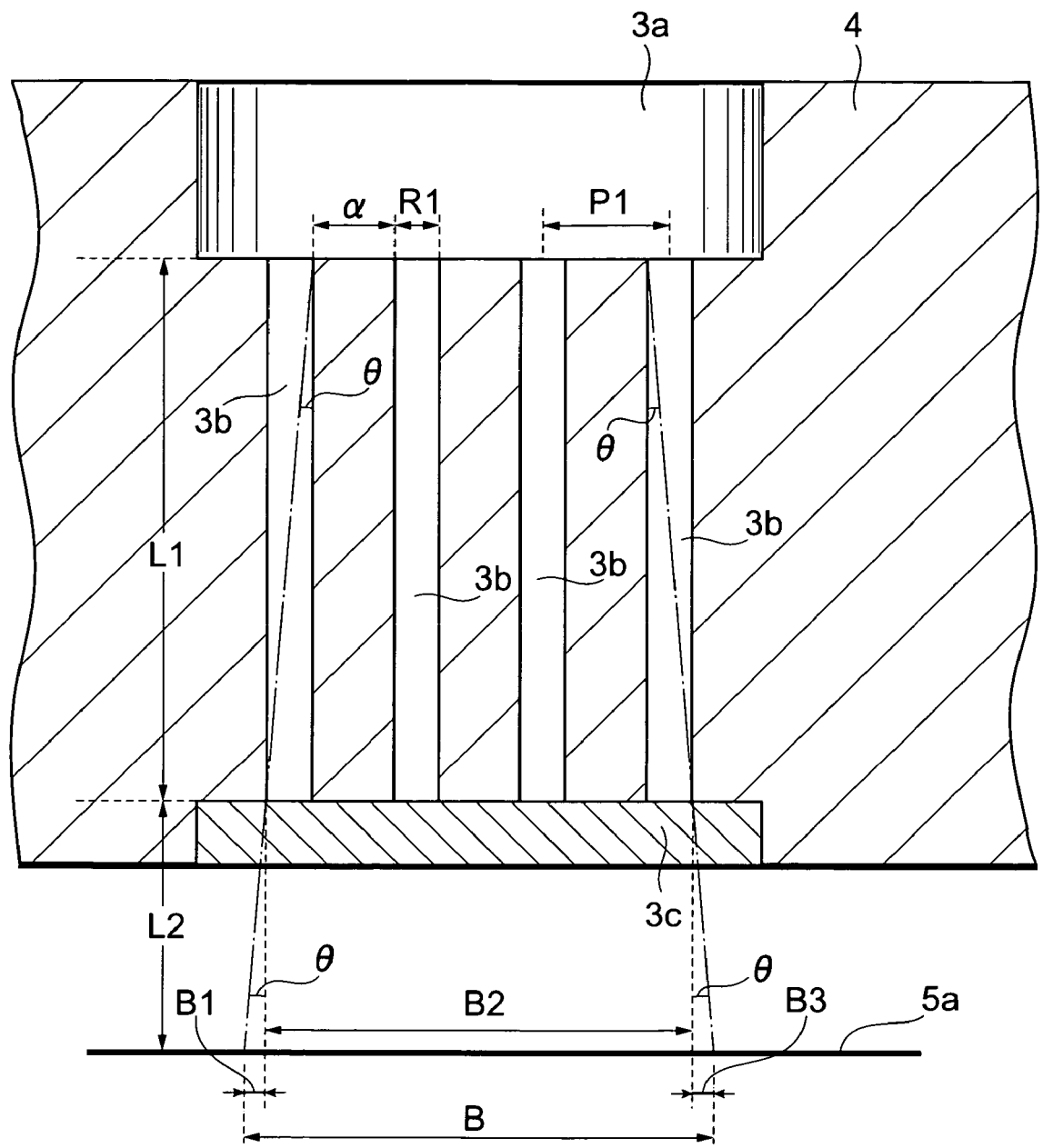
FIG. 6 is an illustration for explaining the number of light guide holes arranged.

Referring to FIG. 6, light entering each light guide hole 3b is light from a region B of the immunochromatographic test strip 5a. Supposing the length of the region B is equal to the length W1 of the colored portion 8, the length of region B2 in which each light guide hole 3b can be set becomes shorter than the length of the region B by the lengths of region B1 and region B3, as shown in FIG. 6. Incidentally, since the length of each of region B1 and region B3 is given by L2×tan θ (=L2×R1/L1), the length of the region B2 where the light guide holes 3b can be set is given by "W1−2×R1×L2/L1."

By dividing the length of region B2 by the pitch P1 at which the light guide holes 3b are arranged, the number N of light guide holes 3b that can be set in the measuring head 4 can be determined as indicated by Formula (2).

Formula (2) is derived by ignoring refraction of light in the protection plate 3c, because the protection plate 3c is formed in a sufficiently small thickness.

The number N of light guide holes 3b to be provided in the measuring head 4 is preferably as large as possible within the range satisfying Formula (2). This configuration increases the amount of reception of the light from the colored portion 8, so as to improve the detection sensitivity.

The pitch P1 is preferably set as small as possible by decreasing the thickness a of the wall between light guide holes 3b. This configuration increases the number N of light guide holes 3b to be set, so as to increase the amount of reception of the light from the colored portion 8, thereby improving the detection sensitivity.

The directivity can be improved by use of a sheet of microblind structure as the protection plate 3c, and it thus becomes feasible to set the inside diameter R1 of light guide holes 3b larger or to set the length L1 of light guide holes 3b shorter.

In the measuring device 1 of the first embodiment, as described above, the plurality of light guide holes 3b, 3b, 3b, 3b are provided along the colored portion 8 of line shape on the immunochromatographic test strip 5a; therefore, even if there is a density difference of color in the colored portion 8, light beams guided from different locations of the colored portion 8 will be averaged, whereby the level of the color of the colored portion 8 can be measured more accurately.

Since the measuring device 1 of the present first embodiment is constructed without use of an imaging lens or the like in the detection optical system 3, the size of the detection optical system 3 can be reduced.

Figure 7:
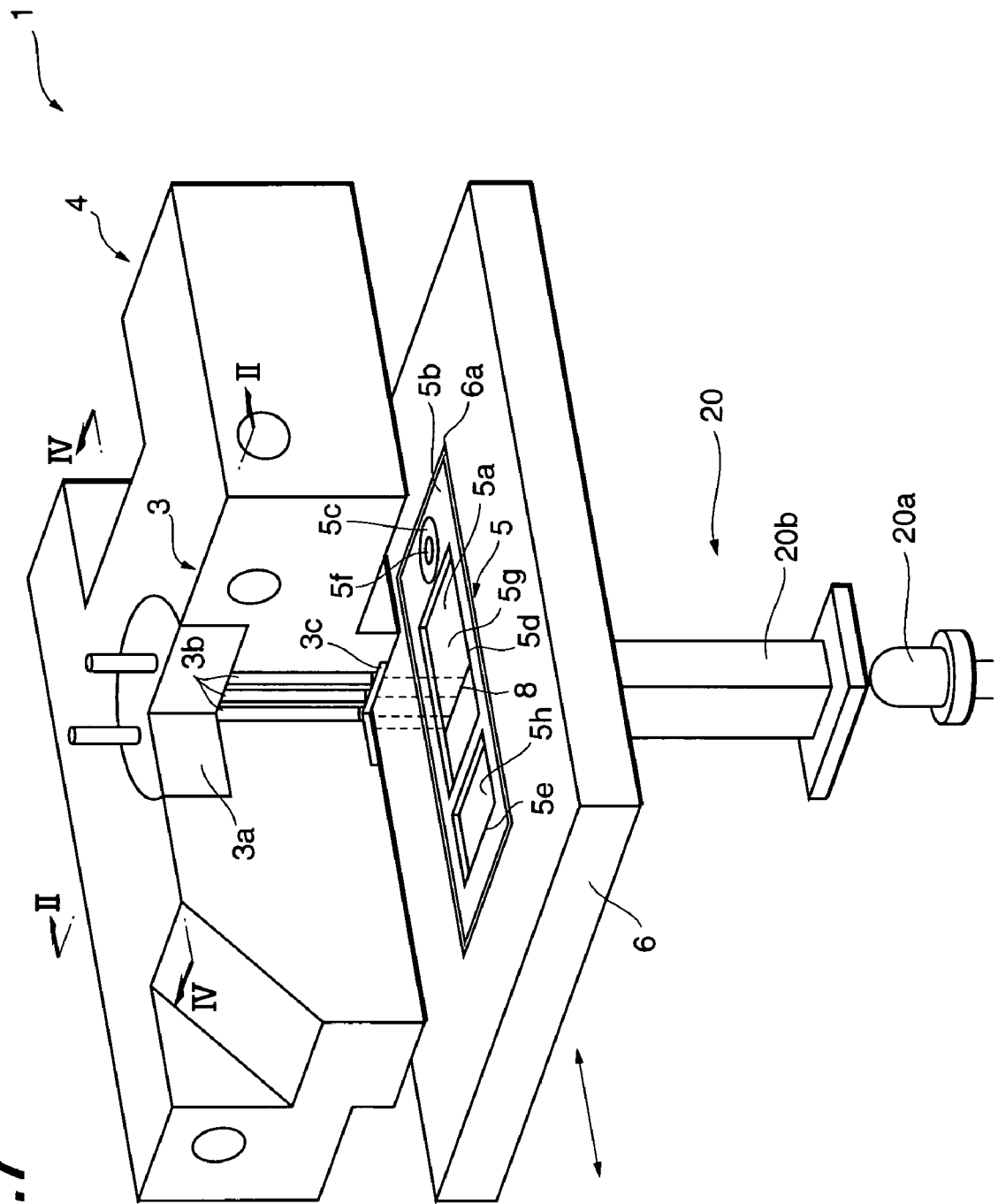
FIG. 7 is a schematic perspective view for explaining a configuration of a modification example of the measuring device for immunochromatographic test strip according to the first embodiment.

As a modification example of the present first embodiment, as shown in FIG. 7, it is also possible to adopt a configuration wherein the irradiation optical system 20 is disposed below the sample table 6, i.e., on the back side of the immunochromatographic test strip 5a. In this case, the measurement light emitted from the LED 20a is uniformized by a mixing rod 20b or the like made in columnar shape and of glass or the like and is irradiated from the back side of immunochromatographic test strip 5a so that transmitted light through the immunochromatographic test strip 5a can be measured by the detection optical system 3. In FIG. 7, the measuring head 4 and others are illustrated as broken in part for convenience' sake of description.

Second Embodiment

Figure 8A:
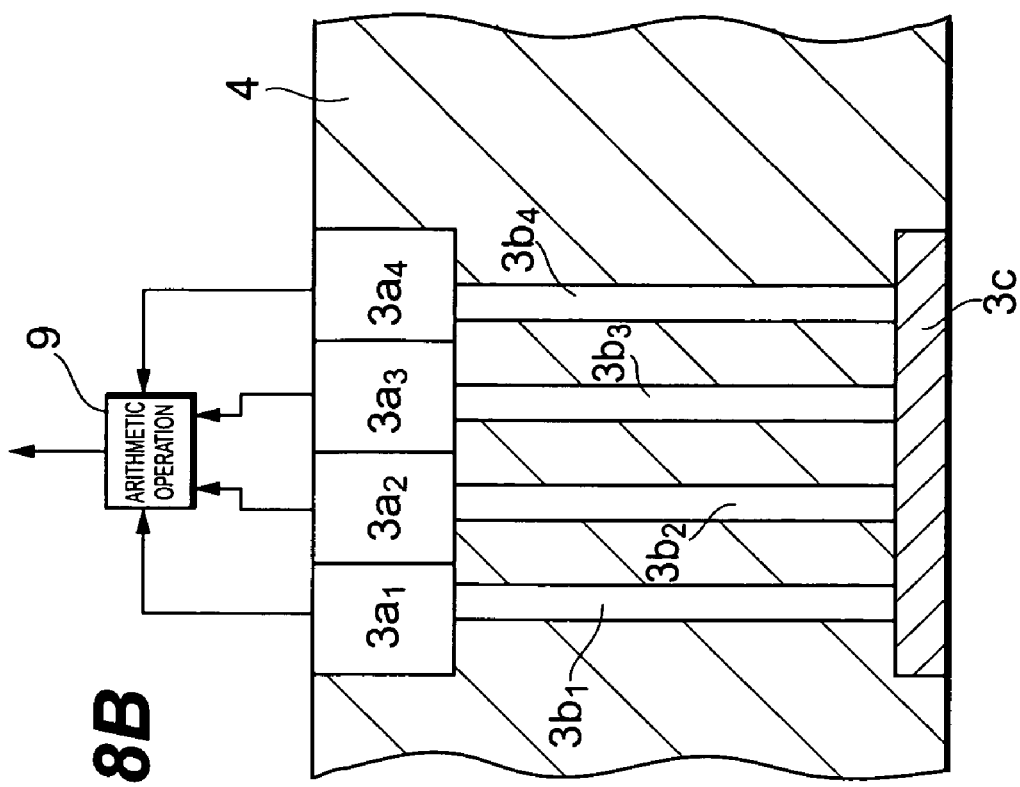
FIG. 8A is a schematic perspective view for explaining a configuration of a measuring device for immunochromatographic test strip according to a second embodiment.
Figure 8B:
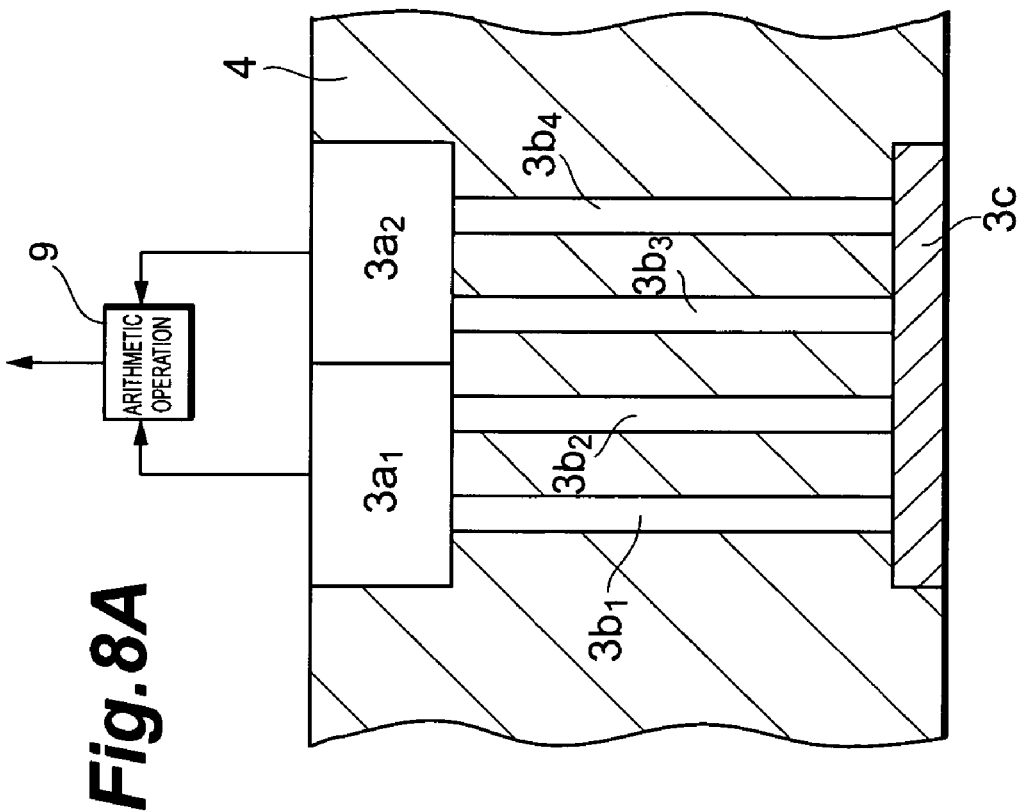
FIG. 8B is a schematic perspective view for explaining a configuration of a measuring device for immunochromatographic test strip according to the second embodiment.

Next, the second embodiment will be described with reference to FIGS. 8A and 8B. FIGS. 8A and 8B are schematic sectional views for explaining configurations of measuring devices for immunochromatographic test strip according to the second embodiment. The present second embodiment is different in the number of photodiodes 3a from the first embodiment.

In the measuring device of the second embodiment, as shown in FIG. 8A, the number of photodiodes is set to 2. Photodiode $3a_1$ is arranged to measure light guided by light guide holes $3b_1$, $3b_2$ and photodiode $3a_2$ is arranged to measure light guided by light guide holes $3b_3$, $3b_4$. The light entering each photodiode $3a_1$, $3a_2$ is converted into an electric output signal by the photodiode $3a_1$, $3a_2$. Output signals from the respective photodiodes are averaged by an arithmetic operation means 9 and the level of the color of the colored portion 8 is calculated based on the average.

In another measuring device of the second embodiment, as shown in FIG. 8B, the number of photodiodes is set to 4. Light beams guided by the respective light guide holes $3b_1$, $3b_2$, $3b_3$, $3b_4$ are measured by different photodiodes $3a_1$, $3a_2$, $3a_3$, $3a_4$, respectively. The light beams entering the respective photodiodes $3a_1$, $3a_2$, $3a_3$, $3a_4$ are converted into electric output signals by the photodiodes $3a_1$, $3a_2$, $3a_3$, $3a_4$. The output signals from the respective photodiodes are averaged by an arithmetic operation means 9 and the level of the color of the colored portion 8 is calculated based on the average.

Since the measuring devices of the present second embodiment are arranged to measure the light from the immunochromatographic test strip 5*a* by the plurality of photodiodes $3a_1$, $3a_2$, $3a_3$, $3a_4$ as described above, the immunochromatographic test strip 5*a* can be evaluated based on the new index of variations in the level of color of colored portion 8 depending upon locations.

Third Embodiment

Next, a measuring device for immunochromatographic test strip according to the third embodiment will be described with reference to FIG. 9. FIG. 9 is a schematic sectional view for explaining a configuration of the measuring device for immunochromatographic test strip of the third embodiment. The present third embodiment is different from the first embodiment in that there are a plurality of detection optical systems provided.

In the measuring device of the third embodiment, a plurality of (two in the present embodiment) detection optical systems $3_1$, $3_2$ are provided in juxtaposition in the measuring head 4. Each of the detection optical systems $3_1$, $3_2$ has a configuration equivalent to the detection optical system 3 of the first embodiment.

Since the measuring device of the present third embodiment enables two immunochromatographic units $5_1$, $5_2$ to be evaluated at the same time and in parallel as described above, the processing speed of immunochromatographic test strips is increased. The number of detection optical systems in the measuring head 4 is not limited to 2, but may be three or more according to need.

INDUSTRIAL APPLICABILITY

The present invention is applicable to measuring devices for immunochromatographic test strips used in pregnancy tests, stool occult blood tests, and so on.

The invention claimed is:

1. A measuring device for immunochromatographic test strip, arranged to irradiate measurement light onto an immunochromatographic test strip and to measure light from the immunochromatographic test strip, the measuring device comprising:
    a table on which the immunochromatographic test strip is to be mounted;
    a photodiode for receiving the light from the immunochromatographic test strip; and
    a light shielding member provided between the immunochromatographic test strip and the photodiode,
    wherein a plurality of hole portions are formed in the light shielding member so as to penetrate the light shielding member from the table side to the photodiode side, whereby a part of the light from the immunochromatographic test strip to the photodiode is guided through each of the hole portions; and
    wherein the plurality of hole portions are juxtaposed along a direction in which a colored portion of line shape formed on the immunochromatographic test strip extends.

2. The measuring device for immunochromatographic test strip according to claim 1, wherein a width of the hole portions is not more than a width of the colored portion of line shape.

3. The measuring device for immunochromatographic test strip according to claim 1, wherein an inside diameter of the hole portions is not more than a width of the colored portion of line shape.

4. The measuring device for immunochromatographic test strip according to claim 1, wherein the number of said photodiode is set to be not less than 1 and not more than the number of said light paths.

5. The measuring device for immunochromatographic test strip according to claim 1, wherein the light from the immunochromatographic test strip is reflected light of the measurement light irradiated onto the immunochromatographic test strip.

6. The measuring device for immunochromatographic test strip according to claim 1, wherein the light from the immunochromatographic test strip is transmitted light of the measurement light irradiated onto the immunochromatographic test strip.

7. The measuring device for immunochromatographic test strip according to claim 1, wherein the immunochromatographic test strip is moved relative to a detection optical system including the photodiode and the light shielding member, in parallel with a moving direction of an antigen or antibody on the immunochromatographic test strip.

8. The measuring device for immunochromatographic test strip according to claim 1, wherein a plurality of photodiodes are juxtaposed alone the direction.

9. A measuring device for immunochromatographic test strip comprising:
    a table on which an immunochromatographic test strip is to be mounted;
    a light emitting diode for emitting light toward the table;
    a photodiode for receiving light coming from the table; and
    a light shielding member disposed between the table and the photodiode,
    wherein the light emitting diode and the photodiode move relative to the table in a predetermined direction, and
    wherein a plurality of hole portions penetrating the light shielding member from the table side to the photodiode side are formed in juxtaposition in a direction intersecting with the predetermined direction, in the light shielding member.

10. The measuring device for immunochromatographic test strip according to claim 1, wherein the photodiode is mounted on the light shielding member.

11. The measuring device for immunochromatographic test strip according to claim 10, further comprising a light emitting diode mounted on the light shielding member,
    wherein a hole portion is formed in the light shielding member so as to penetrate the light shielding member from the light emitting diode side to the table side, whereby the measurement light emitted from the light emitting diode is guided to the immunochromatographic test strip through the hole portion.

12. The measuring device for immunochromatographic test strip according to claim 10, wherein the photodiode and light emitting diode are mounted on the light shielding member, and
    wherein a hole portion penetrating the light shielding member from the light emitting diode to the table side is formed in the light shielding member.

* * * * *